(12) United States Patent
Ayoun et al.

(10) Patent No.: US 8,114,015 B2
(45) Date of Patent: Feb. 14, 2012

(54) LARYNGOSCOPE

(76) Inventors: Gilles Ayoun, Paris (FR); Joel Merran, Paris (FR)

( * ) Notice: Subject to any disclaimer, the term of this patent is extended or adjusted under 35 U.S.C. 154(b) by 978 days.

(21) Appl. No.: 11/993,954

(22) PCT Filed: Jun. 26, 2006

(86) PCT No.: PCT/FR2006/001468
§ 371 (c)(1),
(2), (4) Date: Dec. 26, 2007

(87) PCT Pub. No.: WO2007/003747
PCT Pub. Date: Jan. 11, 2007

(65) Prior Publication Data
US 2008/0200766 A1    Aug. 21, 2008

(30) Foreign Application Priority Data

Jun. 30, 2005   (FR) .................................. 05 06682

(51) Int. Cl.
*A61B 1/267* (2006.01)
(52) U.S. Cl. ......... 600/199; 600/185; 600/193; 600/197
(58) Field of Classification Search ........... 600/184–200
See application file for complete search history.

(56) References Cited

U.S. PATENT DOCUMENTS

| | | | |
|---|---|---|---|
| 3,598,113 A | 8/1971 | Moore | |
| 3,638,644 A | 2/1972 | Reick | |
| 3,771,514 A | 11/1973 | Huffman | |
| 4,815,451 A * | 3/1989 | Bauman | 600/198 |
| 5,060,633 A * | 10/1991 | Gibson | 600/193 |
| 5,277,173 A | 1/1994 | Cantele | |
| 6,036,639 A * | 3/2000 | Allred et al. | 600/193 |
| 6,102,851 A * | 8/2000 | Mellin | 600/199 |
| 6,106,458 A * | 8/2000 | Ha | 600/187 |
| 6,213,937 B1 * | 4/2001 | Vivenzio | 600/199 |
| 6,719,688 B2 * | 4/2004 | Pecherer et al. | 600/199 |
| 7,214,184 B2 * | 5/2007 | McMorrow | 600/185 |
| 2003/0092967 A1 * | 5/2003 | Fourie et al. | 600/191 |
| 2003/0195390 A1 * | 10/2003 | Graumann | 600/188 |

OTHER PUBLICATIONS

International Search Report dated Nov. 16, 2006.

* cited by examiner

*Primary Examiner* — Thomas C. Barrett
*Assistant Examiner* — Michael T Schaper
(74) *Attorney, Agent, or Firm* — Dickinson Wright PLLC

(57) ABSTRACT

According to the present invention, the light source (7) is elastically mounted on the electric housing (5) and it can be pushed back by the projecting proximal end (4P) of the light conduit, when said housing is inserted into the disposable handle (3). As a result of being pushed back, the light source (7) actuates a microswitch (8) which enables it to be powered from a power source (6).

4 Claims, 2 Drawing Sheets

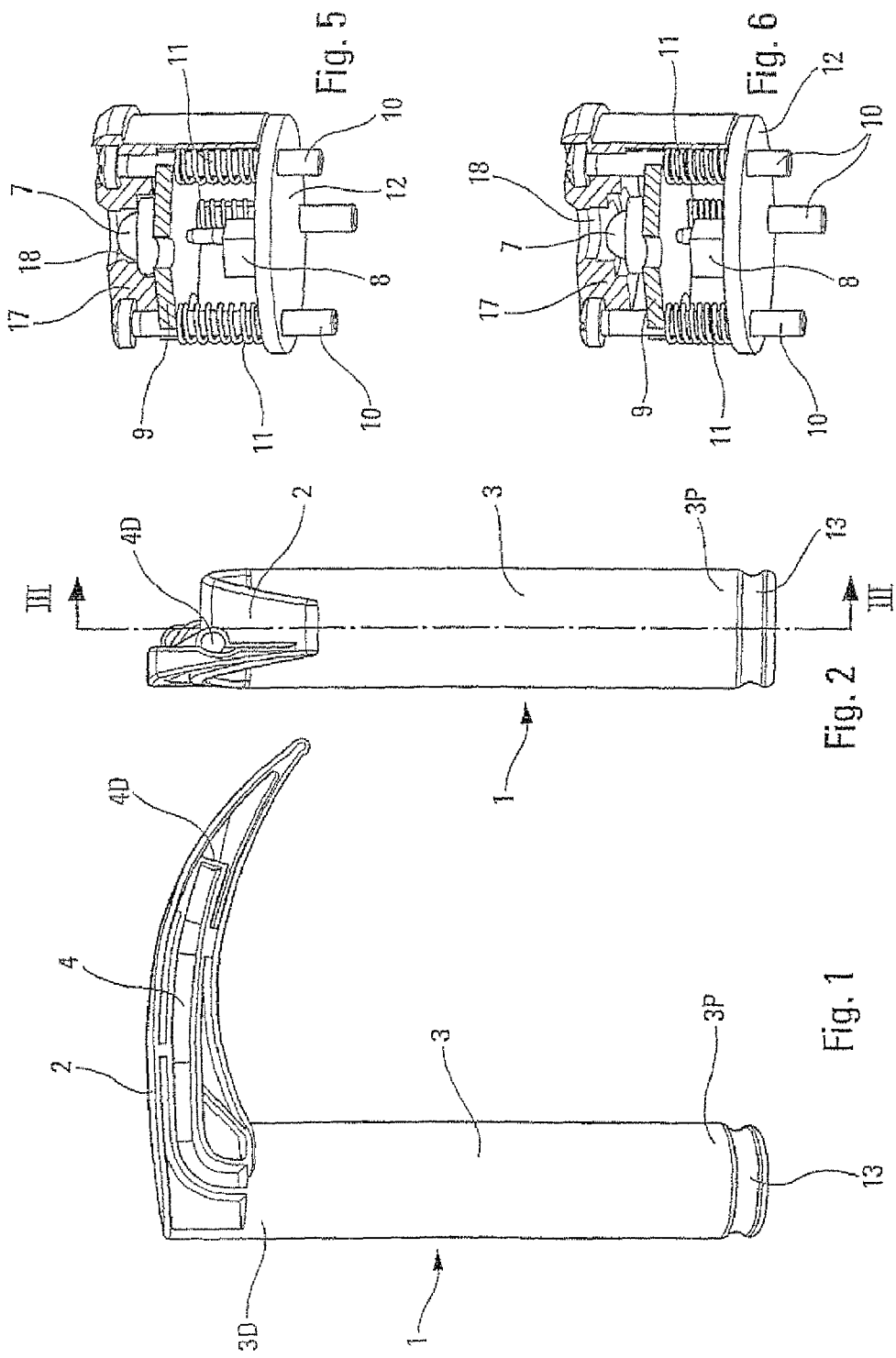

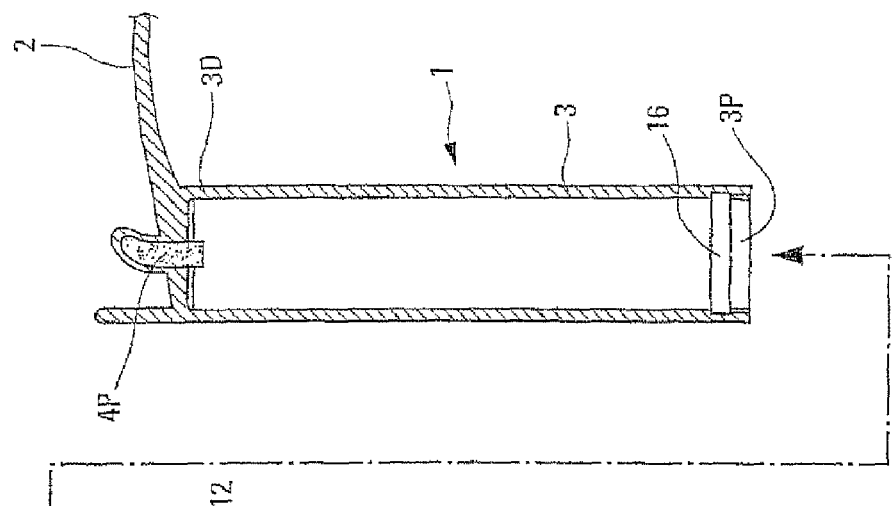
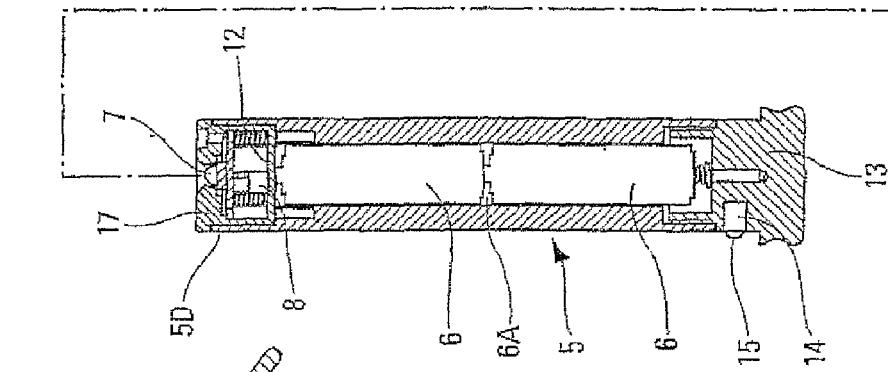
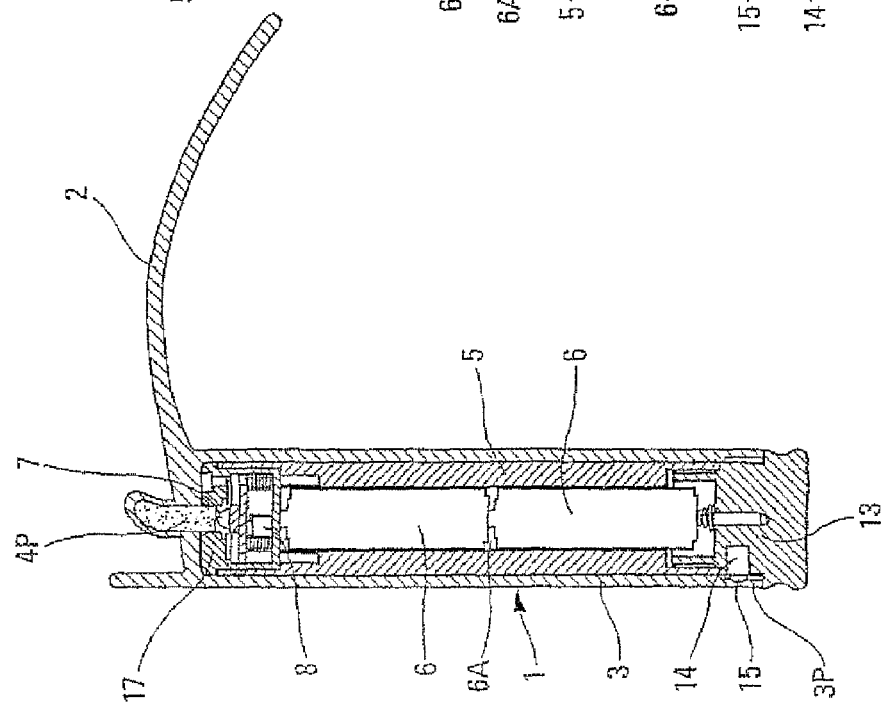
Fig. 3
Fig. 4

LARYNGOSCOPE

The present invention relates to a laryngoscope for medical examination of the larynx of a patient, for example with a view to intubation.

The document U.S. Pat. No. 3,598,113 has already disclosed a laryngoscope comprising:

a component that can be disposed of after use and forms a tongue-depressing blade and a tubular handle, said tongue-depressing blade being arranged at the distal end of said tubular handle and extending transversely with respect to the latter, and the proximal end of said handle being open, said tongue-depressing blade having a light conduit whose proximal end opens into said tubular handle via the distal end thereof supporting said tongue-depressing blade, while the distal end of said light conduit is directed toward the free end of said tongue-depressing blade remote from said tubular handle; and an electrical housing enclosing an electrical power source and having, at its distal end, an electric light source that can be powered from said electrical power source by way of a switch carried by said housing, the latter being able to be introduced into said tubular handle, via said open proximal end thereof, as far as an abutment position in which said electric light source is facing said proximal end of said light conduit.

Such a laryngoscope has the advantage that, during an intervention on a patient, said electrical housing is protected from the latter's saliva by said tubular handle of the disposable component, such that the same electrical housing can be used successively with a plurality of disposable components, optionally having tongue-depressing blades of different sizes. Thus, without risk of contamination of one patient by another, it is possible, for reasons of economy, to use the same electrical housing with a plurality of different successive tongue-depressing blades, each of the disposable components being discarded, for hygiene reasons, after a single use.

In the laryngoscope of document U.S. Pat. No. 3,598,113, said abutment position of the electrical housing in the tubular handle is determined by the cooperation of shoulders provided respectively, on the one hand, on said electrical housing, near the proximal end of said light conduit, and, on the other hand, at the distal end of said housing. Moreover, said switch is provided at the proximal end of the electrical housing and is pressed into the position of powering said light source by the pressure exerted by a screw-on cap, which cooperates with a thread carried by the open proximal end of said handle.

Thus, putting said laryngoscope into operation not only requires the operator to use both hands, but is also not easy. This is because one of the hands has to hold the laryngoscope, while the other screws said cap on until said light source is powered by the electrical power source, by means of closure of said switch.

During an intervention, however, it is rare for the operator to have both hands free at the same time simply to actuate the laryngoscope. Consequently, the use of such a laryngoscope is problematic and risks distracting the operator from another action.

The object of the present invention is therefore to improve the above-described laryngoscope in order to make it particularly easy to use.

To this end, according to the invention, the laryngoscope of the aforementioned type is characterized in that:

said proximal end of said light conduit projects into said tubular handle;

said electric light source is mounted movably on said electrical housing with the aid of elastic means and, in said abutment position, it is in contact with said projecting proximal end of said light conduit which pushes it back counter to the action of said elastic means; and said switch is actuated, in the sense of powering said light source, when the latter is pushed back by said projecting proximal end of said light conduit.

Thus, by virtue of the present invention, it suffices to introduce said electrical housing fully into the tubular handle, such that said light source lights up and illuminates said light conduit. This makes the laryngoscope easier to use.

Advantageously, in order to keep said electrical housing in the tubular handle in the position of illumination of the light source, snap-fit means are provided that mark said abutment position of said housing in said handle.

Said electrical housing preferably comprises, at its distal end, means for guiding the projecting proximal end of said light conduit in the direction of said light source.

The figures of the attached drawing will make it clear how the invention can be realized. In these figures, identical reference numbers designate similar elements.

FIG. 1 is a side view, slightly in perspective, of the laryngoscope according to the present invention.

FIG. 2 is a front view of the laryngoscope in FIG. 1.

FIG. 3 is a sectional view along line III-III in FIG. 2.

FIG. 4 illustrates, in section, the introduction of the electrical housing into the tubular handle of the disposable component.

FIGS. 5 and 6 are perspective views illustrating the placement of the light source in the electrical housing in the unlit position and lit position, respectively.

The embodiment of the laryngoscope according to the present invention, shown in these figures, comprises a disposable component 1, for example made of synthetic material, comprising a tongue-depressing blade 2 and a tubular handle 3. The tongue-depressing blade 2 is arranged at the distal end 3D of the tubular handle 3, transverse thereto. The proximal end 3P of the handle 3 is open (see FIG. 4).

The tongue-depressing blade 2 has a light conduit 4 whose proximal end 4P opens into the tubular handle 3 via the distal end 3D thereof. The distal end 4D of the light conduit 4 is directed toward the free end of the tongue-depressing blade 2 remote from the tubular handle 3.

The laryngoscope shown in the figures moreover comprises an elongate electrical housing 5 with an internal seat 6A for an electric light source 6, for example battery or accumulator, and having, at its distal end 5D, a light source 7, for example a light-emitting diode, which can be supplied with electric current from the electrical power source 6 by way of a microswitch 8 supported by the housing 5.

As is illustrated in FIG. 4, the electrical housing 5 can be introduced into the tubular handle 3 via the open proximal end 3P of the latter.

According to the present invention, and as is shown in FIGS. 3, 4 and 5:

the proximal end 4P of the light conduit 4 projects into the tubular handle 3;

the light source 7 is mounted on a sliding transverse plate 9, which is guided in its sliding movement by longitudinal columns 10 and is pressed elastically by springs 11 in the distal direction 5D of the housing 5;

the distal end 5D of the housing 5 comprises a fixed plate 17 serving as an abutment for the sliding plate 9 pressed by said elastic means 11, and traversed by an orifice 18 through which the projecting proximal end 4P of the light conduit 4 can penetrate and be guided;

said microswitch 8 is arranged between the fixed distal bottom 12 of the internal seat CA of the housing 5 and the sliding plate 9 supporting the light source 7;

the proximal bottom 13 of the housing 5 is in the form of a stopper, for example, and can be removed, for example by screwing, so as to permit access to the seat 6A of the electrical energy source 6; moreover, this proximal bottom 13 comprises, at its periphery, spring-mounted plungers 14 that press balls 15 elastically outward; and near its proximal end 3P, the tubular handle 3 has an inner groove 16 in which the balls 15 can engage.

It will thus be readily understood that, when the housing 6 is introduced all the way into the tubular handle 3, by simple sliding, the proximal end 4P of the light conduit 4 engages in and is guided through the orifice 18 of the fixed plate 17 and comes into contact with the light source 7. As a result, the sliding transverse plate 9 is pushed back counter to the action of the springs 11 and actuates the microswitch 8, which closes the circuit by which the light source 7 is powered by the electrical power source 6 (see FIG. 6 in which the proximal end 4P of the light conduit 4 has been omitted for clarity). At this moment, the balls 15 engage elastically in the groove 16 in order to fix the housing 5 in the abutment position in the handle 3, and part of the proximal bottom 13 of said housing projects outside said handle 3 (see FIGS. 1, 2 and 3).

Thus, the laryngoscope according to the present invention can be automatically started up by simply introducing the housing 5 into the handle 3, for example by sliding it under the action of gravity, the tongue-depressing blade 2 being directed downward.

When the intervention is concluded, said proximal bottom 13 is pulled back in order to withdraw the housing 5 from the handle 3, such that the light source 7 disengages from contact with the proximal end 4P of the light conduit 4 and the springs 11 slacken. The housing 5 then returns to the initial position (see FIG. 5) and is then ready to be introduced into another disposable component 1.

The invention claimed is:

1. A laryngoscope comprising:

a component (1) that can be disposed of after use and forms a tongue-depressing blade (2) and a tubular handle (3), said tongue-depressing blade (2) being arranged at the distal end (3D) of said tubular handle (3) and extending transversely with respect to the tubular handle, and the proximal end (3P) of said handle (3) being open, said tongue-depressing blade (2) having a light conduit whose proximal end (4P) opens into said tubular handle (3) via the distal end (3D) thereof supporting said tongue-depressing blade (2), while the distal end (4D) of said light conduit (4) is directed toward the free end of said tongue-depressing blade (2) remote from said tubular handle (3); and an electrical housing (5) enclosing an electrical power source (6) and an electric light source (7) powered from said electrical power source (6) by way of a switch (8) carried by said housing (5), wherein the electrical housing (5) is included within said tubular handle (3), via said open proximal end (3P) thereof, as far as an abutment position in which said electric light source (7) lies facing said proximal end (4P) of said light conduit (4), wherein:

said proximal end (4P) of said light conduit (4) projects inside said tubular handle (3);

said electric light source (7) being movably mounted with the aid of elastic means (11) and, in said abutment position, the electric light source is in contact with said projecting proximal end (4P) of said light conduit (4), which pushes the electric light source back counter to the action of said elastic means (11); and said switch (8) is actuated, in the sense of powering said light source (7), when the electric light source is pushed back by said projecting proximal end (4P) of said light conduit (4); and, said light source (7) is mounted on a sliding transverse plate (9), which is guided in its sliding movement by longitudinal columns (10) and pressed by said elastic means (11).

2. The laryngoscope as claimed in claim 1, further comprising snap-fit means (14, 15, 16) marking said abutment position of said housing (5) in said tubular handle (3).

3. The laryngoscope as claimed in claim 1, wherein said electrical housing (5) comprises, at its distal end (SD), means (17, 18) for guiding the projecting proximal end (4P) of the light conduit (4) in the direction of said light source (7).

4. The laryngoscope as claimed in claim 3, wherein the distal end (5D) of said electrical housing (5) comprises a fixed plate (17) serving as an abutment for said sliding transverse plate (9) pressed by said elastic means (11), said fixed plate (17) being traversed by an orifice (18) through which the projecting proximal end (4P) of the light conduit (4) can penetrate and be guided.

* * * * *